United States Patent [19]

Polaschegg et al.

[11] Patent Number: 4,702,829
[45] Date of Patent: Oct. 27, 1987

[54] HEMODIAFILTRATION APPARATUS

[75] Inventors: Hans-Dietrich Polaschegg, Oberursel; Bernd Mathieu, Spiesen, both of Fed. Rep. of Germany

[73] Assignee: Fresenius AG, Bad Homburg vdH, Fed. Rep. of Germany

[21] Appl. No.: 806,073

[22] Filed: Dec. 6, 1985

[30] Foreign Application Priority Data

Dec. 7, 1984 [DE] Fed. Rep. of Germany ....... 3444671

[51] Int. Cl.$^4$ .......................... A61M 1/16; A61M 1/34
[52] U.S. Cl. .................................. 210/195.2; 210/259; 210/335; 210/416.1; 210/321.72; 604/5
[58] Field of Search .................. 210/195.2, 259, 321.1, 210/321.2, 321.3, 416.1, 646, 927, 335; 604/4-6

[56] References Cited

U.S. PATENT DOCUMENTS 3,579,441 5/1971 Brown ............................... 210/321.3
4,267,040 5/1981 Schal ................................ 210/321.2
4,338,190 7/1982 Kraus et al. ....................... 210/321.3

FOREIGN PATENT DOCUMENTS 42939 6/1982 European Pat. Off. .
2838414 3/1980 Fed. Rep. of Germany .

OTHER PUBLICATIONS

Miller, "A Volume Controlled Apparatus for Ultrafiltration and Hemofiltration with Acetate or Bicarbonate Solutions," vol. XXV, Trans. Am. Soc. Artif. Intern. Organs, 1979, pp. 404–408.
Henderson, "'On Line' Preparation of Sterile Pyrogen-Free Electrolyte Solution", vol. XXIV, Am. Soc. Artif. Intern. Organs, 1978, pp. 465–467.

Primary Examiner—Richard V. Fisher
Assistant Examiner—W. Gary Jones
Attorney, Agent, or Firm—Townsend and Townsend

[57] ABSTRACT

Hemodiafiltration apparatus (10) comprising a closed dialysis solution cycle which has a balancing system (28), wherein into the closed cycle a first sterile filter (44) is connected from which a connecting line (74, 90, 94) leads to the venous drip chamber (114) of the blood path (102). Connected into said connecting line downstream of the first sterile filter (44) is a substitute pump (76) which is followed downstream by a second sterile filter (78).

8 Claims, 1 Drawing Figure

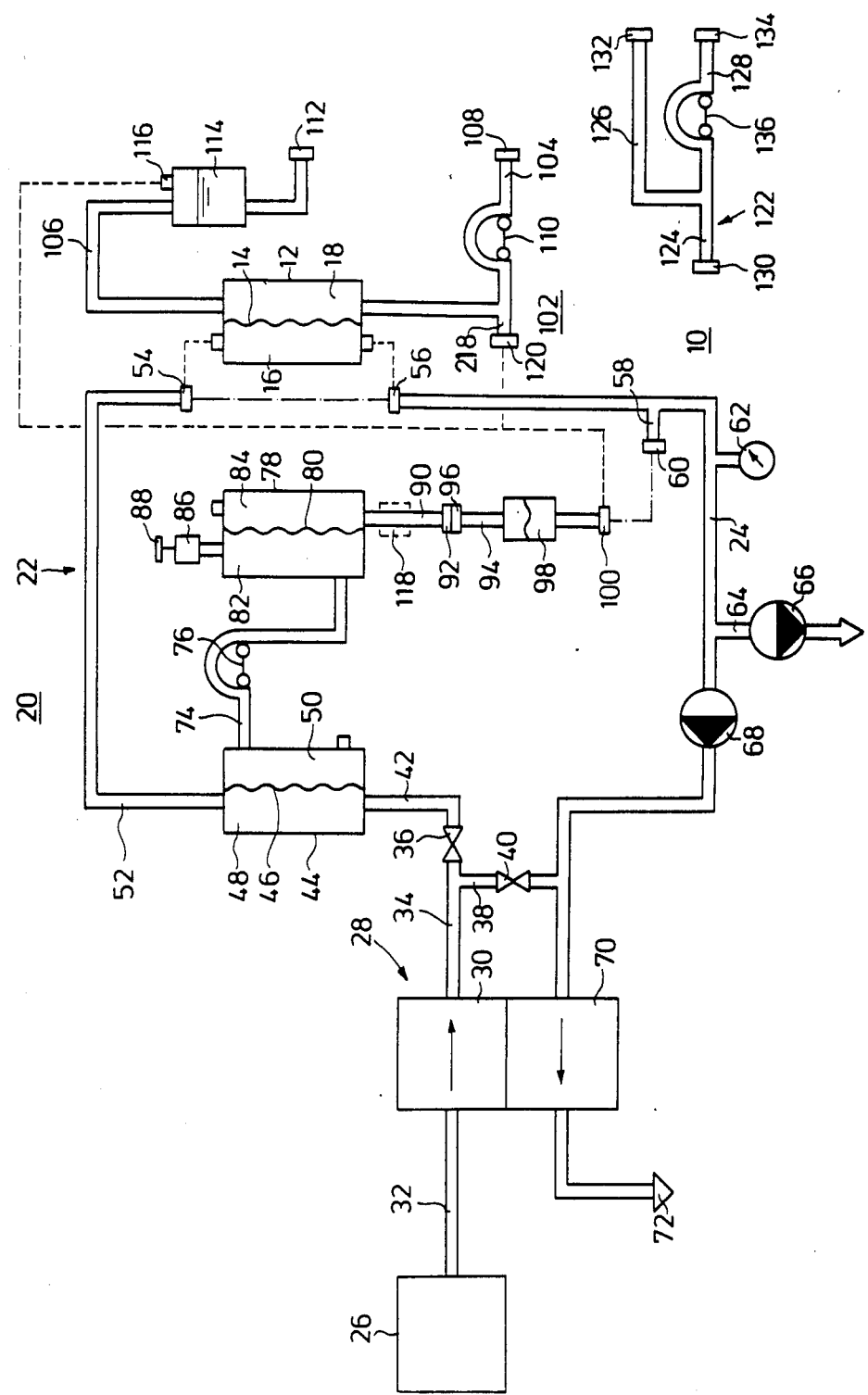

HEMODIAFILTRATION APPARATUS

BACKGROUND OF THE INVENTION

The invention relates to a hemodiafiltration apparatus comprising a dialyzer which is divided by a membrane into two chambers, the first chamber being connected into a dialysis solution path and the second chamber into a blood path, the dialysis solution path comprising a supply line which extends from a means for preparing dialysis solution up to the dialyzer and into which a first balance chamber is connected, and a discharge line which extends from the dialyzer to the discharge and into which a second balance chamber is connected, a pump for conveying dialysis solution in the closed dialysis solution system, an ultrafiltration means provided between the balance chambers in the dialysis solution path, a connecting line which branches from the supply line between the first balance chamber and the dialyzer and which is connected to the blood path and into which at least one sterile filter and a pump are connected, and a drip chamber and a blood pump in the blood path.

In hemodiafiltration, in a manner similar to hemodialysis, blood is conducted past the membrane of a hemofilter, part of the serum being withdrawn via the membrane. This part is replaced by a sterile substitution liquid which is added to the extracorporeal blood path either upstream of the dialyzer (predilution) or downstream of the dialyzer (postdilution). In addition, in the diafiltration the usual hemodialysis is carried out, i.e. at the membrane of the hemodialyzer dialysis solution is led past so that across the membrane an exchange of substances usually eliminated with urine can take place.

Generally, at present substitute solutions are made available by manufacturers who produce infusion solutions and the like. Accordingly, relatively large-volume containers are made by the manufacturer which contain sterile and pyrogen-free substitute and thereafter brought to the patient, this involving high costs with the result that due to said high substitute costs hemofiltration has not been able to establish itself particularly well.

For this reason attempts have already been made to produce the substituate solution on-line, i.e. at the bedside, in that the usual dialysis solution is transformed to the sterile and pyrogen-free state and the substituate thereby obtained thereafter administered to the patient.

From the Trans. Am. Soc. Artif. Intern. Organ (ASAIO), 1978, p. 465–467, the on-line production of a sterile and pyrogen-free substituate is known which is made by employing the usual proportioning unit for making the conventional dialysis solution. A concentrate is mixed in a ratio of 1:34 with water, the dialysis solution thereby produced degassed and heated and thereafter supplied to two ultrafilters which are connected in series. At the end of the second filter sterile and pyrogen-free substituate is obtained which is then supplied to the blood path.

In this preparation procedure the delivery pump is thus upstream of the two ultrafilters which has however not been found expedient. For the delivery pump is on the pressure side of the first filter and thus conveys the particles and germs contained upstream of the ultrafilters in the dialysis solution under pressure into the first ultrafilter. This results in the so-called closed-end effect, i.e. the particles conveyed under pressure rapidly clog the ultrafilter and consequently this arrangement has not proved itself in practice. DE-OS No. 3,407,147 discloses an apparatus for preparing medical infusion solutions in which a concentrate liquid and pure water are mixed together in a mixing container in a predetermined ratio. After the mixing the mixture obtained is applied with the aid of a pump to only one ultrafilter so that in this case as well the same disadvantages as in the arrangement mentioned above occur, i.e. the socalled closed-end effect again results.

From ASAIO 1979, p. 404–408, a further on-line substituate producing unit is known which corresponds substantially to the unit explained above, i.e. once again two ultrafilters are disposed in the dialysis solution path. In addition, however, downstream of these two filters a delivery pump is connected into the substituate delivery path but this is also disadvantageous because the pressure drop across the two ultrafilters is too high and as a result these pumps operate in the vacuum region. A consequence of this is that the usually flexible substituate stituate solution is no longer possible. In addition, this substituate is again degassed and this is extremely undesirable for medical reasons.

EP-OS No. 42,939 discloses a hemofiltration system which proceeds from the apparatuses mentioned above with the provision that only one ultrafilter is used for sterilizing the dialysis solution. This filter must be specially monitored to detect immediately any leak occurring. This relatively complicated apparatus is eliminated in the aforementioned systems by the provision of two filters, which for economic reasons is substantially more advantageous and moreover technically simpler.

SUMMARY OF THE INVENTION

The invention is therefore based on the problem of further developing a hemodiafiltration apparatus of the type mentioned at the beginning so that the ultrafilters have a high operating life and the pressure drop in the region of the ultrafilters does not lead to a vacuum.

The solution of this problem is effected in that the substituate pump is connected between the sterile filters.

The substituate pump according to the invention is disposed downstream of the first sterile filter and upstream of the second sterile filter, i.e. it is connected on the reduced pressure side to the first sterile filter whilst the excess pressure side is directed towards the second sterile filter.

As a result the aforementioned closed-end effect is avoided with the apparatus according to the invention because the particles are no longer pressed into the filter pores. Consequently, the membranes of the first sterile filter have a considerably longer service life, i.e. clogging does not occur until after a considerably longer time.

Due to the removal of the particles in the first sterile filter at the most a few pyrogens are conveyed by the pump to the second sterile filter so that the latter cannot be clogged by particles. The purpose of this second filter is moreover only to intercept any leak occurring in the first filter, i.e. keeping the particles and germs then passing through away from the patient to be treated.

Thus, from this point of view the substituate pump can be disposed in the pressure region of the second sterile filter without the latter clogging. Consequently, the closed-end effect is no longer of any significance.

The interposition of the substituate pump between the two sterile filters further has the advantage that the pressure balance between the two sterile filters is equalized and as a result the aforementioned vacuum when the substituate pump is disposed downstream of the two sterile filters does not arise. Consequently, the substituate pump according to the invention can also be used with the usual pumping rate without any risk of a vacuum occurring which could lead to further degassing of the dialysis solution.

As a result, the hemodiafiltration apparatus according to the invention produces a sterile and pyrogen-free substituate solution for the hemofiltration, neither a closed-end effect nor a vacuum at the two sterile filters due to the action of the substituate pump occurring.

According to the invention the first and second sterile filters are ultrafilters having a very high separating power, i.e. these filters have a separating limit of at the most 40000 Dalton thus, they do not allow molecules with a higher molecular weight to pass. In this respect these ultrafilters differ from the conventional microporous sterile filters which generally have a pore size of about 0.2 $\mu$m and can only keep back bacteria but cannot filter off endotoxins (pyrogens) or other very fine particles.

According to a preferred embodiment the first sterile filter is constructed as highly permeable ultrafilter. This is intended to ensure a high flow of dialysis solution through the filter, i.e. the suction power of the substituate pump when using such a sterile filter can be kept relatively low.

Advantageously a semipermeable membrane is used which has a water permeability of about 30–600 ml/($m^2$ h mmHg), in particular about 100–300 ml/($m^2$h mmHg). According to the invention it is advantageous for this first sterile filter to have a considerably higher water permeability than the second sterile filter. The ratio of the water permeability of the first sterile filter compared with the second sterile filter should lie in a range from 2:1 to 6:1, in particular at about 4:1.

Furthermore, the total surface area of the first sterile filter may be small compared with the second sterile filter, for example about half the surface of the second sterile filter. A surface area of about 1–1.5 $m^2$ has been found advantageous.

One example of a first sterile filter of this type is the dialyzer F60 sold by Applicants which has a water permeability of about 210 ml/$hm^2 \times$ mm Hg and a membrane surface area of about 1.2 $m^2$.

The particles and germs are effectively held back at this first sterile filter without any danger of clogging or blockage. Furthermore, due to the highwater permeability it is not necessary to set a particularly high suction pressure at the substituate pump.

Compared with the first sterile filter the second sterile filter, as already mentioned above, may have a lower water permeability but should have a greater surface area. In this second sterile filter any pyrogens which might pass the first sterile filter should be removed substantially by adsorption and this is made possible preferably by narrow pores and the greatest possible exchange area. In addition, the second sterile filter is to provide the aforementioned safety function on membrane failure of the first sterile filter.

A second sterile filter has been found advantageous which has a water permeability of about 30–90, in particular 50–70 ml/$hm^2$, and a surface area of about 1.5–3, in particular about 2 $m^2$. Such a filter is marketed for example by Applicants under the designation D6.

For the sterile filters according to the invention conventional membrane materials are used, for example Cuprophan or polysulfone.

Furthermore, apart from the usual dialysis filters as second sterile filter so-called deep filters can be used which have a high surface, thereby increasing the ability to adsorb pyrogens.

The sterile filter according to the invention is to be regarded as redundant because the first and second sterile filters monitor each other and any fault which occurs first can be detected with certainty by a pressure drop at the manometer provided in the dialysis solution, that is the rinsing liquid, circuit. For safety, advantageously between the treatments a pressure test as described below is carried out with which the intact undamaged state of the sterile filters can be checked.

Thus, in this respect according to the invention monitoring of the intact condition of the two sterile filters by a pressure means in the dialysis solution circuit is provided during the preparation of the hemofiltration solution as well as a check of the two sterile filters between the treatments.

Thus, due to its redundancy the arrangement according to the invention must be regarded as safe and consequently the hemofiltration solutions prepared are both sterile and free from pyrogens.

Further details, features and advantages of the invention will be explained with the aid of the following description of an example of embodiment with reference to the drawing.

BRIEF DESCRIPTION OF THE DRAWING

The drawing shows a schematic illustration of a hemodiafiltration apparatus having two sterile filters between which a substituate pump is disposed.

DETAILED DESCRIPTION

In the FIG. 10 denotes a hemodiafiltration apparatus which comprises a conventional dialyzer 12 which is divided by a membrane 14 into a chamber traversed by the dialysis solution or rinsing liquid 16 and a chamber 18 traversed by the blood.

The chamber 16 is connected into a dialysis solution path 20 which consists of a supply line 22 and a discharge line 24.

Whereas the one end of the supply line 22 is connected to the inlet of the dialyzer 12 the other end of the supply line 22 is connected to a unit 26 for preparing dialysis solution.

This unit 26 prepares the conventional dialysis solution, for example on a bicarbonate basis.

Also connected into the supply line 22 is a balance chamber 30 belonging to the balance unit 28. Said balance chamber 30 is connected on the one hand via the conduit section 32 to the unit 26 for preparing the dialysis solution and on the other hand via a conduit section 34 to a dialyzer valve 36 connected into the supply line 22. Branching from the conduit section 34 upstream of the dialyzer valve 36 is a bypass conduit 38 into which a bypass valve 40 is inserted and which is connected to the discharge line 24.

Branching from the dialyzer valve 36 is a further conduit section 42 which is connected to a first sterile filter 44. Said sterile filter is divided by a membrane 46 into a first chamber 48 and a second chamber 50.

Branching from the outlet of the first chamber 48 is a further conduit section 52 which can be connected to the inlet of the dialyzer 12 with the aid of a connector 54 disposed at its end. In the drawing this connector 54 is shown in the non-connected condition whilst the connected condition is indicated by a dashed line.

Branching off downstream of the chamber 16 is the discharge line 24 which can be connected to the chamber 16 via a connector 56 disposed at the end of the discharge line 24.

As indicated by dot-dash line, the two connectors 54 and 56 can be connected, i.e. the supply line 22 and the discharge line 24 can be shortcircuited, bypassing the dialyzer 12.

Furthermore, from the discharge line 24 a connecting line 58 branches whose end is provided with a connector 60 which is sealed in the unattached condition. The discharge line 24 is further connected to a manometer 62, via a branching line 64 to an ultrafiltration means 66 and to a circulation pump 68.

Finally, downstream of the connection of the discharge line 24 to the bypass line 38 the second balance chamber 70 of the balance chamber system 28 is connected into the discharge line 24 and is followed by the drain 72 of the discharge 24.

Consequently, the line system extending from the balancing unit 28 and led through the dialyzer 12 represents a hydraulically closed unit as already described in DE-PS No. 2,838,414, to which reference is made and which is made part of the subject of this description.

As already mentioned above, in the supply line 22 a first sterile filter 44 is disposed. Branching from the second chamber of said sterile filter 44 is a connecting line 74 into which a substituate pump 76 is connected and which is connected to a second sterile filter 78.

Said second sterile filter comprises a membrane 80 which divides the second sterile filter 78 into a first chamber 82 and a second chamber 84. The first chamber 82 is connected to the connecting line 74. Furthermore, the first chamber 82 is connected to an equalization chamber 86 whose upper end is sealed with a hydrophobic bacteria-repelling microfilter 88.

The second chamber 84 of the second sterile filter 78 comprises a discharge line 90 which has at its end a connector 92. Said discharge line 90 can be connected to a further conduit section 94 via a complementary connector 96 into which a further microfilter 98 is incorporated. The membrane provided in said microfilters advantageously has a pore size of about 0.2 μm. Finally, the end of the conduit section 94 is provided with a connector 100 complementary to the connector 60.

The conduit section 94, the connector 96, the microfilter 98 and the connector 100 form a dispensable article to be used only once.

The chamber 18 of the dialyzer 12 traversed by the blood comprises a blood path 102 which is mde up of a supply line 104 and a discharge line 106. The supply line 104 comprises at its end a connector 108 which can be connected to the body of the patient. Furthermore, a blood pump 110 is incorporated in the supply line 104.

The discharge line 106 comprises at its end likewise a connector 112 which can in turn be connected to the body of the patient. Furthermore, both connectors 108 and 112 may be combined to form one connector (single needle).

Also connected into the discharge line 106 is a venous drip chamber 114 which includes at the top thereof a connector 116 which is complementary to the connector 100 of the substituate conduit.

The hemodiafiltration apparatus 10 is operated in the following manner:

Dialysis solution is first prepared in the usual manner by the unit 26. The balance chamber 30 delivers per stroke a predetermined volume of dialysis solution into the closed cycle, it being assumed that the dialyzer valve 36 is open and the bypass valve 40 closed. The balanced dialysis solution amount flows through the conduit section 42, the first chamber 48 of the sterile filter 44, the conduit section 52, the first chamber 16 of the dialyzer 12 and the discharge line 24 to the second balance chamber 70 and from there to the drain 72. The balance chamber 70 conveys the same volume out of the closed cycle.

In addition, the ultrafiltration apparatus 66 can be operated. Due to the constant volume of the dialysis solution cycle the amount of solution pumped off via the ultrafiltration means 66 is removed directly from the blood cycle through the membrane 14 of the dialyzer 12.

This mode of operation corresponds to a conventional hemodialysis as described for example in DE-PS No. 2,838,414.

To carry out a hemodiafiltration the connector 100 is connected to the venous drip chamber 114 via the connector 116. This establishes a direct connection between the supply line 22 of the dialysis solution cycle and the blood path 102. This direct connection thus exists via the connecting line 74, the discharge line 90 and the conduit section 94, these lines being connected in each case to the sterile filter 44 and 78 and the microfilter 98 respectively.

The substituate pump 76 is now set into operation at a predetermined pumping rate. Consequently, a predetermined amount of dialysis solution is sucked from the first chamber 48 through the member 46 into the second chamber 50 of the first sterile filter 44, passes from there through the connecting line 74 into the first chamber 82 of the second sterile filter 78, from where it passes through the membrane 80' into the second chamber 84 of the sterile filter 78 and finally through the discharge line 90, the conduit section 94 and the microfilter 98 connected into the conduit section 94 into the venous drip chamber 114 as indicated by the dotdash line (connection of the connectors 100 and 116). It is however also conceivable for the conduit section 94 to be connected upstream of the dialyzer 12 to the blood path 102 as also indicated by the dashed line.

As already explained above the dialysis solution cycle between the balancing system 28 and the dialyzer 12 represents a closed system. By the action of the substituate pump 76 from said closed system a predetermined amount of solution is withdrawn which is necessarily in turn taken from the flood through the membrane 14. Consequently, from the blood of the patient in the dialyzer 12 a predetermined amount of serum fluid is removed which is replaced downstream of the dialyzer in the venous drip chamber 114 by an equivalent amount of substituate solution (diafiltration). However, in similar manner, as already explained above, it is also possible to add upstream of the dialyzer a certain amount of substituate solution to the blood, which is removed again in the dialyzer.

Now, it has been found that in the first sterile filter the particles can be effectively held back without clogging occurring after several treatments or without any danger of an appreciable performance drop in the first sterile filter 44.

Furthermore, in the second sterile filter 78 the pyrogens allowed to pass by the first sterile filter 44 are trapped with the result that no secondary effects due to pyrogens could be observed in the patient.

By the interposition of the substituate pump between the two sterile filters 44 and 78 the reduced pressures or partial vacuums with which the two sterile filters must be operated are not added together. This would lead as already explained at the beginning downstream of the two sterile filters due to the summation of the individual partial vacuums to a total reduced pressure leading to an undesirable further degassing of the substituate solution and moreover to collapse of the tubing system.

Apart from the diafiltration, with the hemodiafiltration apparatus according to the invention a conventional ultrafiltration may be carried out with the aid of the ultrafiltration apparatus 66 so that not only the blood can be "washed" with the substituate solution but in addition a predetermined ultrafiltration amount can be withdrawn from the blood.

As explained below, this hemodiafiltration apparatus 10 can be sterilized, flushed, tested and vented in the following manner:

Sterilization

It is assumed that dialysis and flushing has been carried out previously; on initial setting up or changing of the sterile filters 44 and 78 the first operation is "venting". For this purpose the connector 100 is connected to the connector 60. At the same time the dialysis solution cycle is shortcircuited by connecting the two connectors 54 and 56.

The blood system itself is out of operation. The hemodialysis apparatus 10 is now sterilized in accordance with the sterilization programme, the substituate pump 76 being operated at a predetermined rate, for example about 200 ml/min. Advantageously, the substituate pump 76 operates in synchronism with the bypass valve 40 which is out of step with the dialyzer valve 36. Consequently, the substituate pump 76 sucks disinfectant solution prepared by the unit 26 from the first sterile filter 44 into the second sterile filter 78 in which the liquid level in the balance chamber 86 is up to the hydrophobic microfilter 88. Thereafter, disinfectant solution is pressed out of the second sterile filter 78 through the microfilter 98 into the discharge line 24 of the dialysis solution path 20. Thus, in this sterilizing step the balancing in the closed system is retained.

Flushing

Thereafter the hemodiafiltration appratus 10 is switched to "flushing", the unit 26 now making available fresh water. Flushing is carried out until the disinfectant solution has with certainty been removed from the entire system by the fresh water.

Testing

To check the hemodiafiltration apparatus 10 the flexible connecting line 74 is removed from the substituate pump 76. Otherwise, the aforementioned arrangement is retained (shortcircuiting; without switching on of the dialyzer). To check whether the two sterile filters 44 and 78 are intact, with the balance chamber system 28 disconnected the ultrafiltration pump 66 is set in operation. Since the closed system is now only connected to the surroundings via the hydrophobic microporous microfilter 88, air flows into the first chamber 82 of the second sterile filter 78 and through the line 74 into the second chamber 50 of the first sterile filter 44. Since the two membranes 46 and 80 of the two sterile filters 44 and 78 are wetted with water the inspired air can cannot escape via the wetted filters and this thereby provides a possibility of checking for any cracks in the membranes 46 and 80 with the aid of the vacuum generated by the ultrafiltration pump 66. This vacuum can be followed at the manometer 62.

When the dialysis solution cycle is intact and the sterile filters are also intact, after reaching a partial vacuum of about 520 mm Hg a certain time (for example about 2 min) is allowed to pass. Thereafter the pressure at the manometer 62 is observed and the time measured which the pressure needs to rise from a partial vacuum of about 500 to 400. If this time is greater than about 1 minute the sterile filters 44 and 78 are considered tight. Should the time be less either one or both of the filters and/or the dialysis solution system has a leak. This step is practically identical to the first step of the pressure maintenance test for checking that the balancing system is intact.

Venting

After the test stage venting takes place, i.e. the entire system is filled again with dialysis solution. For this purpose the connector 100 remains at the connecting line 58 disposed downstream of the dialyzer in the discharge line 24 whilst the connecting line 74 is again connected to the substituate pump 76. The supply line 22 and discharge line 24 remain shortcircuited. The balance chamber system 28 is operated with a normal program and the unit again makes dialysis solution available.

Furthermore, the blood side is filled with physiological saline solution in that the two connectors 108 and 112 are connected to a bag filled with saline solution and the blood pump 110 started up. This bag must contain enough solution to enable the entire blood system to be filled therewith, and in addition a reserve of about half a litre saline solution should remain in the bag.

As soon as the supply line and discharge line 22 and 24 are filled with dialysis solution, the two chambers 50 and 82 of the sterile filters 44 and 78 remaining filled with air, the shortcircuiting connection between the connectors 54 and 56 is removed, the latter being connected to the chamber 16 of the dialyzer 12. Furthermore, the connector 100 is separated from the connector 60, the latter thereby being sealed.

The dialysis solution cycle is now switched on again and the substituate pump 76 operated with a predetermined rate (about 100–200 ml/min). The end of the microfilter 98 or connector 100 remains open and is brought into a position which lies above that of the hydrophobic microfilter 88. Furthermore, the connector 100 is connected to a collection container because solution will emerge from the microfilter 98.

In normal operation of the balancing system 28 the substituate pump 76 first pumps the air out of the chambers 50 and 82 through the hydrophobic microporous microfilter 88, the air volume removed being simultaneously replaced by dialysis solution drawn from the chamber 44. Because of the constant volume of the closed system a corresponding amount is removed by ultrafiltration from the chamber 18 of the dialyzer 12, i.e. directly from the bag with saline solution.

After the removal of the air from the chamber 50 the air is also expelled from the chamber 82 through the microfilter 88. The equalization chamber 86 provided between the chamber 82 and the sterile filter is intended to prevent the hydrophobic microfilter 88 being sealed by the very first solution drops.

As soon as the chamber 82 is completely filled with dialysis solution or substituate solution, liquid comes out of the microfilter 98. The substituate pump 76 and the blood pump 110 are stopped when said emerging liquid is substantially free from air. Thereafter the connection between the connectors 92 and 96 is separated, the microfilter 98 discarded and replaced by a new microfilter. Thereafter the new connector 100 is connected to the venous drip chamber 114 via the connector 116.

To ensure that this method functions at the very beginning of the filling phase the blood cycle must be started up in order to recirculate the saline solution. Possibly, prior to replacing the microfilter 98 and connecting the connector 100 to the venous drip chamber 114 a sample can be taken and checked for sodium content, or the conductivity determined. For this purpose it is possible to provide permanently a conductivity cell as indicated by dashed line at 118 in the discharge line 90.

As mentioned above, the substituate pump 76 is advantageously a peristaltic hose pump. On the other hand, however, instead of such a hose pump a pump of a different type may be used, for example a gear pump not fully occluding. In this case for the checking it is no longer necessary to remove the flexible tubing from the pump. Consequently, both the supply tubing and the discharge tubing remain connected to such a pump.

As shown in the Figure the connector 100 can be connected both to the connector 116 of the drip chamber 114 (postdilution) and to the supply line 104 downstream of the blood pump 110. For this purpose from the supply line 104 a flexible tube 218 branches which is provided with a connector 120. Said connector 120 can be connected both to the connector 92 of the discharge line 90 and to the connector 100 in complementary manner.

In such a case predilution is then present.

According to a further embodiment both predilution and postdilution may be carried out, the substituate solution produced being correspondingly divided. For this purpose a y-shaped conduit section 122 is provided in which the main branch 124 divides into the two side branches 126 and 128. Each of these branches 124–128 is provided at its end with a connector 130, 132 and 134.

The connector 130 can be connected either to the connector 92 or the connector 100 whilst the connectors 132 and 134 can be connected to the connector 116 of the drip chamber 114 and the connector 120 of the supply line 104 respectively.

To be able to use the substituate flow generated both for the predilution and for the postdilution at least one pump is connected into one of the side branches 126 or 128. As shown in the Figure a pump 136, preferably constructed as peristaltic pump, is connected into the predilution side branch 128. Said pump 136 takes from the total substituate flow a predetermined subflow whilst the remainder is conducted through the second side branch 126 to the drip chamber 114. However, on the ohter hand the pump 136 may also be connected into the other branch 126 or two pumps can be provided in both side branches.

According to a further embodiment the pump 136 can be dispensed with if the pump 76 is constructed as peristaltic double hose pump. In this case one of the side branches 126 or 128 is placed together with the hose-like connecting line 74 into the hose pump 76, and it is to be ensured that due to the differences of the hose internal diameter or hose cross-section the ratio of the total flow to the subflow is defined.

We claim:

1. Hemodiafiltration apparatus comprising a dialyzer (12) which is divided by a membrane into two chambers, the first chamber being connected into a dialysis solution path (22) and the second chamber into an extracorporeal blood path (104, 106) of a patient, the dialysis solution path comprising a supply line (32, 34, 42, 52, 22) which extends from a means for preparing dialysis solution (26) up to the dialyzer (12) and through which a first balance chamber (30) is connected, and a discharge line (24) which extends from the dialyzer (12) to a drain (72) and through which a second balance chamber (70) is connected, a circulation pump (68) for conveying dialysis solution in the dialysis solution path, a connecting line (74) which branches from the supply line (22) between the first balance chamber (30) and the dialyzer (12) and which is connected to the blood path (104, 106), and a drip chamber (114) and a blood pump (110) in the blood path (104, 106), the improvement comprising:

a first sterile ultrafilter (44) provided between the dialysis solution path (22) and the connecting line (74), a second sterile ultrafilter (78) provided in the connecting line (74), and a substituate pump (76) connected between the first and second sterile ultrafilters (44, 78) for supplying hemofiltration replacement fluid to replace lost ultrafiltrate caused by action of said substituate pump (76) to the blood path.

2. Apparatus according to claim 1, the improvement further comprising the first sterile ultrafilter having a greater water permeability than the second sterile ultrafilter (78).

3. Apparatus according to claim 1 or 2, the improvement further comprising the second sterile ultrafilter (78) having a greater membrane surface area than the first sterile ultrafilter (44).

4. Apparatus according to claim 1, the improvement further comprising a substitution fluid chamber (82) and an equalizer chamber (86), said substitution fluid chamber (82) of the second sterile filter (78) terminating said connecting line (74), said substitution fluid chamber being subjected to the inflowing substitute solution, said substitution fluid chamber being connected to said equalizing chamber (86) which is sealed by a hydrophobic microfilter (88), said equalizing chamber for protecting said hydrophobic microfilter from blockage by liquid.

5. Apparatus according to claim 1, the improvement further comprising in the discharge line (24) of the dialysis solution path a branching connecting line (58) is provided which comprises at its end a connector (60) which is connectable to a connector (100) from an outlet of said second ultrafilter.

6. Apparatus according to claim 1, the improvement further comprising the supply line (22) and the discharge line (24) of the dialysis solution path (20) each having at their end a connector (54; 56) and said connectors being connectable either together to form a short circuit or to the first chamber (16) of the dialyzer (12).

7. Apparatus according to claim 1, the improvement further comprising venous drip chamber (114) provided in the discharge line (106) of the blood path (102) comprising a connector (116) which is connectable to a connector (100) from an outlet of said second ultrafilter.

8. Apparatus according to claim 1, the improvement further comprising said second ultrafilter having a second chamber separated from a first chamber (82) by a sterile filter membrane (80), the second chamber (84) of the second sterile ultrafilter (78) being connected via a y-shaped branching conduit (122) having side branches (126, 128) to the blood path (104, 106) and a pump (136) being connected on one of the two side branches (126, 128) for pumping hemofiltration replacement fluid at a predetermined ratio between a predilution input (at 102) and a postdilution input (at 116) into the blood path.

* * * * *